United States Patent
Harczos

(10) Patent No.: US 9,409,016 B2
(45) Date of Patent: *Aug. 9, 2016

(54) ELECTRODE STIMULATION SIGNAL GENERATION IN A NEURAL AUDITORY PROSTHESIS

(75) Inventor: Tamas Harczos, Wümbach (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 114 days.

This patent is subject to a terminal disclaimer.

(21) Appl. No.: 13/601,419

(22) Filed: Aug. 31, 2012

(65) Prior Publication Data

US 2013/0231714 A1 Sep. 5, 2013

Related U.S. Application Data

(63) Continuation of application No. PCT/EP2010/069525, filed on Dec. 13, 2010.

(60) Provisional application No. 61/310,425, filed on Mar. 4, 2010.

(51) Int. Cl.
*A61N 1/05* (2006.01)
*A61N 1/36* (2006.01)

(52) U.S. Cl.
CPC ........... *A61N 1/36032* (2013.01); *A61N 1/0541* (2013.01)

(58) Field of Classification Search
CPC ............ A61N 1/0541; A61N 1/36032; A61N 1/36178; A61B 5/6817

USPC .......................... 607/55–57, 73, 136
See application file for complete search history.

(56) References Cited

U.S. PATENT DOCUMENTS

| | | |
|---|---|---|
| 4,905,285 A | 2/1990 | Allen et al. |
| 6,064,913 A | 5/2000 | Irlicht et al. |
| 6,915,264 B2 | 7/2005 | Baumgarte |
| 6,944,501 B1 * | 9/2005 | Pless ............................... 607/45 |
| 7,039,466 B1 | 5/2006 | Harrison et al. |

(Continued)

FOREIGN PATENT DOCUMENTS

WO 2009/143553 A1 12/2009

OTHER PUBLICATIONS

Official Communication issued in International Patent Application No. PCT/EP2010/066525, mailed on Apr. 13, 2011.

(Continued)

*Primary Examiner* — Eugene Wu
(74) *Attorney, Agent, or Firm* — Keating & Bennett, LLP

(57) ABSTRACT

An auditory stimulation signal processing device includes a plurality of signal inputs adapted to receive a plurality of frequency bin signals; a signal selector adapted to select a selected frequency bin signal from the plurality of frequency bin signals; a parameter modifier adapted to vary at least one stimulation signal generation parameter used for generating an electrode stimulation signal and affecting a shape of a basic stimulation pulse; and an electrode stimulation signal generator adapted to generate the electrode stimulation signal for application to an electrode of a neural auditory prosthesis, the electrode corresponding to a frequency of the selected frequency bin signal. A corresponding method and a computer readable digital storage medium are also disclosed.

13 Claims, 11 Drawing Sheets

(56) References Cited

U.S. PATENT DOCUMENTS

| | | | |
|---|---|---|---|
| 7,050,856 B2* | 5/2006 | Stypulkowski | 607/45 |
| 7,076,308 B1 | 7/2006 | Oversteet et al. | |
| 7,130,694 B1 | 10/2006 | Voelkel | |
| 7,317,945 B2 | 1/2008 | Litvak et al. | |
| 7,321,797 B2* | 1/2008 | Blamey et al. | 607/57 |
| 8,000,797 B1* | 8/2011 | Sarpeshkar et al. | 607/57 |
| 8,180,445 B1* | 5/2012 | Moffitt | 607/2 |
| 8,265,767 B2* | 9/2012 | Lineaweaver | 607/57 |
| 2003/0135248 A1* | 7/2003 | Stypulkowski | 607/73 |
| 2003/0167077 A1 | 9/2003 | Blamey et al. | |
| 2005/0222641 A1* | 10/2005 | Pless | 607/45 |
| 2006/0080087 A1* | 4/2006 | Vandali et al. | 704/207 |
| 2006/0195160 A1* | 8/2006 | Blamey et al. | 607/57 |
| 2006/0271127 A1* | 11/2006 | Voelkel | 607/57 |
| 2008/0319509 A1 | 12/2008 | Laback et al. | |
| 2009/0024185 A1 | 1/2009 | Kulkarni et al. | |
| 2009/0030486 A1 | 1/2009 | Klefenz | |
| 2009/0319005 A1* | 12/2009 | Lineaweaver | 607/57 |

OTHER PUBLICATIONS

Rouger et al., "Evidence that Cochlear-Implanted Deaf Patients are Better Multisensory Integrators," PNAS, vol. 104, No. 17, Apr. 24, 2007, pp. 7295-7300.

Sumner et al., "A Revised Model of the Inner-Hair Cell and Auditory-Nerve Complex," J. Acoust. Soc. Am., vol. 111 No. 5, Pt. 1, May 2002, pp. 2178-2188.

Harczos et al., "Formant Map Counterpart in Auditory Processing Based on Cochlear Pressure Wave Trajectories," Proc. IEEE Biomed., Circuits and Systems, 2008, pp. 45-48.

Harczos et al., "Towards Automatic Speech Recognition Based on Cochlear Traveling Wave Delay Trajectories," Int. Symposium on Auditory and Audiology Research, 2007, Helsingor, Denmark, pp. 1-8.

Harczos et al., "Evaluation of Cues for Horizontal-Plane Localization with Bilateral Cochlear Implants," Int. Symposium on Auditory and Audiology Research, 2009, Helsingor, Denmark, pp. 1-8.

Baumgarte, "Ein Psychophysiologisches Gehörmodell zur Nachbildung Von Wahrnehmungsschwellen für die Audiocodierung," PhD Dissertation, Universität Hannover, Germany, 2000, 179 pages.

Zwicker et al., "Cochlear Preprocessing in Analog Models, in Digital Models and in Human Inner Ear," Hearing Research, vol. 44, 1990, pp. 209-216.

Johnstone et al., "Basilar Membrane Measurements and the Travelling Wave," Hearing Research, vol. 22, 1986, pp. 147-153.

Elberling et al., "Auditory Steady-State Responses to Chirp Stimuli Based on Cochlear Traveling Wave Delay," J. Acoust. Soc. Am., vol. 122, 2007, No. 5, pp. 2772-2785.

Loizon, "Mimicking the Human Ear," IEEE Signal Processing Magazine, vol. 7, No. 5, Sep. 1998, pp. 101-130.

Harcozos, "Method and Apparatus for Generating an Electrode Stimulation Signal in a Neural Auditory Prosthesis," U.S. Appl. No. 13/601,012, filed Aug. 31, 2012.

* cited by examiner

ELECTRODE STIMULATION SIGNAL GENERATION IN A NEURAL AUDITORY PROSTHESIS

CROSS-REFERENCE TO RELATED APPLICATIONS

This application is a continuation of copending International Application No. PCT/EP2010/069525, filed Dec. 13, 2010, which is incorporated herein by reference in its entirety, and additionally claims priority from U.S. Application No. 61/310,425, filed Mar. 4, 2010, which is also incorporated herein by reference in its entirety.

BACKGROUND OF THE INVENTION

Embodiments of the invention relate to a method and an apparatus for generating an electrode stimulation signal in a neural auditory prosthesis. In embodiments of the invention, a randomizer is controlling a generation of the electrode stimulation signal to vary in a random manner within a certain allowable range.

The field of the present invention relates to an auditory prosthesis, like a cochlear implant or a brainstem implant, configured for delivery of non-simultaneous stimulation through at least two active electrodes.

The global deaf population is roughly estimated to be 0.1% of the total population. There are various causes of deafness including infectious, traumatic, toxic, age-related, occupational, and genetic disorders. In the majority of the cases the inner ear, i.e. the cochlear structure, is damaged.

Nowadays, however, there are ways to bypass the peripheral auditory system and directly stimulate auditory nerve fibers. This process is made available by the cochlear implants (CIs), which have been the target of intensive research for over fifty years by now, and by the more recent brainstem implants (BIs). Even though cochlear implants are the most successful neural prosthesis ever, hearing can only be partially restored by them. Patients achieve an average of almost 80% in speech recognition tests under quiet conditions (without lip-reading) until the end of the second year after implantation (cf. the article "Evidence that cochlear-implanted deaf patients are better multisensory integrators" by Rouger et al., published in Proc. Nat. Acad. of Sciences (PMAS), vol. 104 (17), pp. 7295-7300, 2007 and in Journal of Acoust. Soc. Am., vol. 111 (5), Pt. 1, May 2002), but most cochlear implant recipients remain unable to enjoy music or to distinguish among complex sounds. Moreover, speech recognition in noisy environments is still a challenge for most cochlear implant recipients.

Even today a number of modern CI systems employ speech processing strategies that are still based on very "simple" filter-banks (e.g. the Fast Fourier Transform (FFT), dating back to the mid-1960s) to mimic the complex functionality of the human auditory system. On the other hand, numerous biologically motivated models of the basilar membrane (BM, organ of the cochlear filtering) and of auditory structures—having strong non-linear properties beyond the BM have been developed during the last 20 years.

Recent research of the inventor indicates that time has come for practical CI/BI systems and theoretical ear models to converge and facilitate a higher quality of restoration of hearing.

U.S. Patent Application Publication No. 2009/0030486 A1 discloses a method of generating a control signal for a cochlear implant based on an audio signal. An activity pattern over time at a plurality of inner ear cells of an auditory model is calculated. Activity events within the activity pattern are filtered out based on a recognition of a characteristic pattern in the activity pattern, whereby cleared information is obtained. The cleared information is further used as a control signal for the cochlear implant, or the control signal for the cochlear implant is derived from the cleared information. The idea disclosed in the '486 U.S. patent application is based on the knowledge that in an activity pattern, a multitude of activity impulses is present at a plurality of inner ear cells of an auditory model over a time, which are not relevant for a patient's auditory sensation. Thus, a characteristic pattern in the nerve activity pattern can be recognized and, based on the recognition of the characteristic pattern, some of the activity events can be filtered out because they are only of secondary importance for a patient's perception. An example of the recognition of the characteristic pattern is a Hough-based pattern classification.

A hearing prosthesis configured for delivery of stochastic stimulation to a recipient is disclosed in U.S. Patent Application Publication No. 2009/0319005 A1. A stochastic stimulation generator is configured to generate a stochastic sequence of stimulation pulses having first and second inter-pulse intervals distributed stochastically throughout the sequence within controlled limits. Thus, the temporal positions of the stimulation pulses are subject to random variations, but the basic shape of a stimulation pulse is predetermined.

U.S. Patent Application Publication No. 2008/0319509 A1 discloses a similar approach as the '005 U.S. Patent Application Publication. In US 2008/0319509 A1 a binaural stimulation in a neural auditory prosthesis or hearing aid is disclosed. A phase jitter component is added to the binaural stimulation signal to reduce the periodic characteristics of the fine structure component by preserving the interaural time difference (ITD) information. Again, the temporal position of the basic pulses is varied at random, while a shape of each basic pulse remains constant.

SUMMARY

According to an embodiment, a method of generating a control signal for a neural auditory prosthesis may have the steps of: receiving a plurality of frequency bin signals; selecting a selected frequency bin signal from the plurality of frequency bin signals; varying at least one stimulation signal generation parameter used for generating an electrode stimulation signal and affecting a shape of a basic stimulation pulse, the at least one stimulation signal parameter representing a duration of a phase gap between a positive and a negative pulse of a biphasic pulse, wherein varying the at least one stimulation signal generation parameter is a random process; and generating the electrode stimulation signal for application to an electrode of the neural auditory prosthesis corresponding to a frequency of the selected frequency bin signal, the generating of the electrode stimulation signal using the at least one stimulation signal generation parameter subject to variations.

According to another embodiment, a computer readable digital storage medium having stored thereon a computer program having a program code for performing, when running on a computer, a method for signal processing of a signal in a neural auditory prosthesis, wherein the method may have: receiving a plurality of frequency bin signals; selecting a selected frequency bin signal from the plurality of frequency bin signals; varying at least one stimulation signal generation parameter used for generating an electrode stimulation signal and affecting a shape of a basic stimulation pulse, the at least one stimulation signal parameter representing a duration of a phase gap between a positive and a negative pulse of a biphasic pulse, wherein varying the at least one stimulation signal generation parameter is a random process; and generating the electrode stimulation signal for application to an electrode of the neural auditory prosthesis corresponding to a frequency of the selected frequency bin signal, the generating of the electrode stimulation signal using the at least one stimulation signal generation parameter subject to variations.

According to another embodiment, an auditory stimulation signal processing device may have: a plurality of signal inputs adapted to receive a plurality of frequency bin signals; a signal selector adapted to select a selected frequency bin signal from the plurality of frequency bin signals; a parameter modifier adapted to vary at least one stimulation signal generation parameter used for generating an electrode stimulation signal and affecting a shape of a basic stimulation pulse, the at least one stimulation signal parameter representing a duration of a phase gap between a positive and a negative pulse of a biphasic pulse, the parameter modifier including a randomizer for randomizing the varying of the at least one stimulation signal generation parameter; and an electrode stimulation signal generator adapted to generate the electrode stimulation signal for application to an electrode of a neural auditory prosthesis, the electrode stimulation signal corresponding to a frequency of the selected frequency bin signal.

According to an embodiment, a method of generating a control signal for a neural auditory prosthesis may have the actions of: receiving a plurality of frequency bin signals; selecting a selected frequency bin signal from the plurality of frequency bin signals; varying at least one stimulation signal generation parameter used for generating an electrode stimulation signal and affecting a shape of a basic stimulation pulse; and generating the electrode stimulation signal for application to an electrode of the neural auditory prosthesis corresponding to a frequency of the selected frequency bin signal, the generating of the electrode stimulation signal using the at least one stimulation signal generation parameter subject to variations.

According to another embodiment, an auditory stimulation signal processing device may have: a plurality of signal inputs adapted to receive a plurality of frequency bin signals; a signal selector adapted to select a selected frequency bin signal from the plurality of frequency bin signals; a parameter modifier adapted to vary at least one stimulation signal generation parameter used for generating an electrode stimulation signal and affecting a shape of a basic stimulation pulse; an electrode stimulation generator adapted to generate the electrode stimulation signal for application to an electrode of a neural auditory prosthesis, the electrode corresponding to a frequency of the selected frequency bin signal.

Another embodiment may have a computer program having program code for performing, when running on a computer, a method of generating a control signal for a neural auditory prosthesis as mentioned above.

In embodiments of the invention, an amplitude equalization may be performed on the received plurality of frequency bin signals. Hence, the auditory stimulation signal processing device may further comprise an amplitude equalizer adapted to perform an amplitude equalization on the received plurality of frequency bin signals.

Embodiments of the invention are based on the recognition that a degree of randomness in the electrode stimulation signal or the control signal relative thereto is likely to add to a bio-compatibility of the electrode stimulation signal. A possible explanation is that the neural auditory prosthesis interfaces with a remaining, healthy part of the recipient's auditory sense which is used to, or genetically predetermined, receiving nervous stimuli from a natural, now defunct part of the auditory sense.

In embodiments of the disclosed teachings, the plurality of frequency bin signals may be received from a filter bank based on a stimulation of at least one of a basilar membrane and an inner hair cell.

In embodiments of the disclosed teachings the method may further comprise:
determining whether an electrode of the neural auditory prosthesis had been selected for stimulation during a previous stimulation cycle; and
attenuating a corresponding frequency bin signal that corresponds to the determined electrode stimulated during the previous stimulation cycle.

In the case of an auditory stimulation signal processing device, this functionality may be provided by the amplitude equalizer, i.e, the amplitude equalizer may be adapted to determine whether one electrode of the neural auditory prosthesis had been selected for stimulation during at least one previous stimulation cycle among a certain number of previous stimulation cycles and to attenuate a corresponding frequency bin signal that corresponds to the determined electrode stimulated during the previous stimulation cycle among the certain number of the last stimulation cycles. In the alternative to the amplitude equalizer, this functionality or an equivalent functionality may be provided by another component of the auditory stimulation signal processing device.

In embodiments of the teachings disclosed herein, the method may comprise further actions prior to assigning the selection probability values to a plurality of frequency bin signals. One of these actions may be a mapping of an amplitude of each one of the plurality of frequency bin signals to a loudness-map representation of the amplitude, the mapping being based on patient-specific conditions.

The auditory stimulation signal processing device may further comprise a loudness mapping function connected to the signal input and adapted to map an amplitude of at least one of the plurality of frequency bin signals to a loudness-mapped representation of the amplitude, the mapping being based on patient-specific conditions.

In embodiments of the disclosed teachings, the parameter modifier may comprise a randomizer so that the variation of the stimulation signal generation parameter is based on a random process.

In embodiments of the disclosed teachings, the stimulation signal generation parameter may affect a waveform of the electrode stimulation signal. In particular, a template for creating the electrode stimulation signal may comprise a temporal gap in which the template is substantially zero-valued between two non-zero sections. The stimulation signal generation parameter subject to random variation may be a duration of the temporal gap between the two non-zero sections.

In the following specification, the neural auditory prosthesis will be described as a cochlear implant. It is, however, clear for a person skilled in the art that it is possible to employ the inventive approach with other types of neural auditory prostheses.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
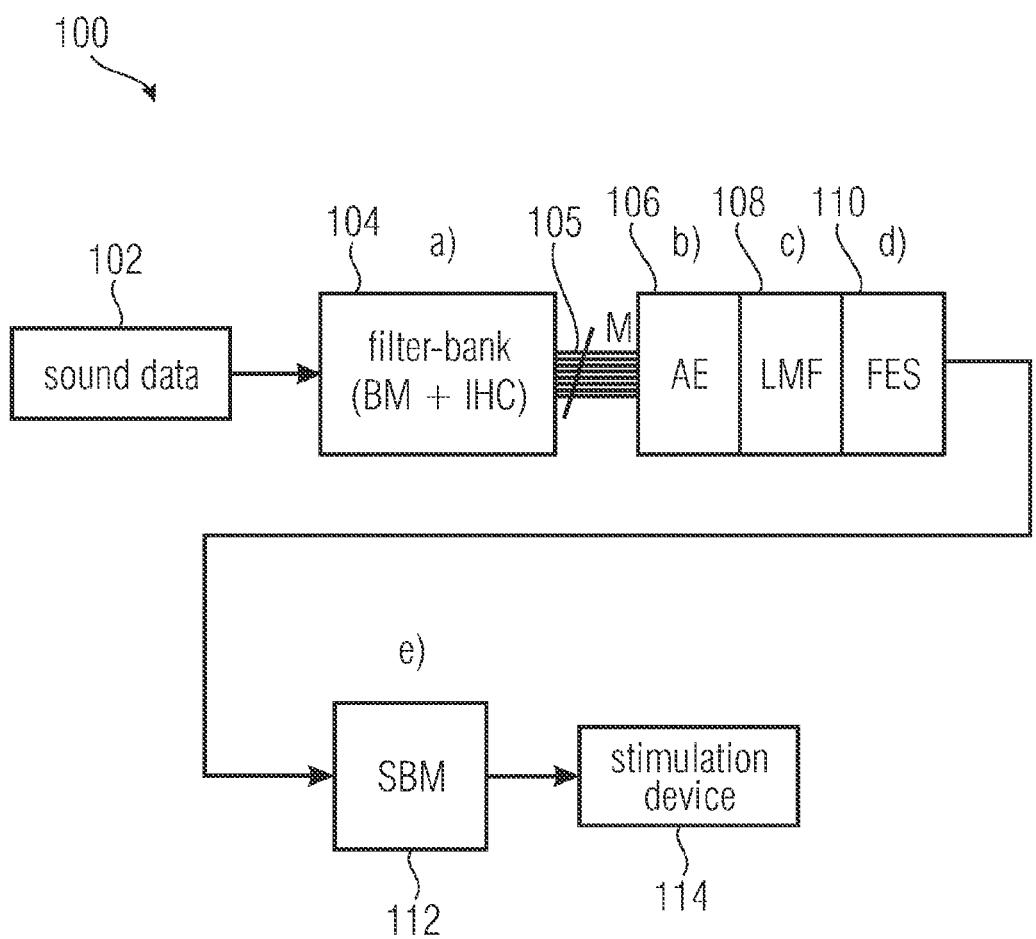
FIG. 1 is a schematic block diagram illustrating an overview of a neural auditory prosthesis.

FIG. 1 shows a schematic block diagram of a neural auditory prosthesis 100 in which some of the main components are illustrated. Generally, the neural auditory prosthesis 100 receives a sound signal, processes the sound signal, and generates an electrical stimulation signal. Depending on the anatomical site where the electrical stimulation signal stimulates a recipient's nervous tissue, the neural auditory prosthesis 100 may comprise a cochlear implant (CI), a brainstem implant (BI), or another type of implant. In the case of a cochlear implant a stimulation device 114 is implanted in the cochlea of the recipient. In the case of a brainstem implant, the stimulation device 114 may comprise electrodes that are implanted near the surface of the cochlear nucleus of the brainstem.

The auditory neural prosthesis 100 typically receives an audio signal at an audio signal interface 102, which generates sound data corresponding to the audio signal. The audio signal interface 102 may comprise a microphone, an amplifier, and an analog-to-digital converter. The sound data is transmitted to a filter bank 104 which may be based on a simulation model of the basilar membrane (BM) and/or a simulation model of the inner hair cells (IHC). The filter bank 104 analyzes the sound data with respect to frequency contents of the sound data falling into a plurality of frequency ranges. The filter bank 104 may be based on a computer simulation of a basilar membrane model, or it could be based on e.g. a Fast Fourier transform. The filter bank 104 has M output bands, each of the output bands containing a frequency bin signal of a plurality of frequency bin signals 105. In an exemplary implementation of the filter bank 104 a frequency resolution is set to 0.25 Bark/band, which results in 101 bands over the whole audible range. A sampling rate is set to 44100/s in this exemplary implementation. Next, only the M of 101 bands are kept, which have characteristic frequencies (CF) closest to the corresponding electrode channels' characteristic frequencies. Typically, the characteristic frequencies of the electrode channels are approximately logarithmically spaced over the frequency and span over a typical cochlear implant frequency range, i.e. from approximately 250 Hz to 7500 Hz. In another possible implementation different from the mentioned exemplary implementation, the filter bank 104 could provide the desired number of M bands directly that are matched to the characteristic frequencies of the electrode channel of a cochlear implant or a brainstem implant. Hence, no selection of frequency bands is necessitated anymore in order to reduce the number of frequency bands from e.g. 101 to M, and no superfluous filtering of unused frequency bands needs to be carried out.

Besides a computer simulation of a basilar membrane model, the filter bank 104 may further comprise a computer simulation of an inner hair cell model, which acts like a rectifier with non-linear properties.

In this exemplary implementation, the complete filter bank 104 provides a set of output data (one sample per band) for each stimulation cycle. If the total stimulation rate (TSR) is not equal to the sampling rate, then the filter bank output may be resampled to the total stimulation rate. The set of output data forms the plurality of frequency bin signals 105.

An amplitude equalizer 106 (AE) is adapted to equalize the plurality of frequency bin signal 105 corresponding to the filter bank bands in a way that the plurality of frequency bin signals 105 has the same range of magnitude among all bands. For example, the amplitude equalizer 106 may adjust the plurality of frequency bin signals 105 so that the output range of each band is in [0,1], where 0.0 and 1.0 are extremes corresponding to a pure tone input with the center frequency of the given band at 25.0 and 65.0 dB SPL model perception level, respectively. Optionally, the amplitude equalizer 106 may have an input and a memory regarding which electrode of the stimulation device 114 was selected for stimulation in the last stimulation cycle, or in one of the last stimulation cycles. If an electrode L was selected for stimulation in the last stimulation cycle, then the frequency bin signal of the frequency band that corresponds to the electrode L stimulated in (one of) the last cycle(s), will be attenuated for the current stimulation cycle by a certain amount, e.g. 10.0 dB. It is believed that the attenuation increases safety by decreasing the risk of over stimulation by repetition, and/or supports the perception of onsets, which may lead to better speech perception.

The equalized frequency bin signals are forwarded to a loudness mapping function 108 which maps the amplitude of the samples to an electrical unit representing the magnitude of the stimulation. The low and high limit of the stimulation magnitude per electrode is individual among CI-patients. Assuming the patient's limits are $C_{low}$ and $C_{high}$, the loudness mapping function 108 will map the input range of [0, 1] to $[C_{low}, C_{high}]$. The loudness mapping provided by the loudness mapping function 108 can be non-linear, but has to be monotonic. In an exemplary embodiment which has been implemented for test purposes, the loudness mapping is linear.

Figure 3:
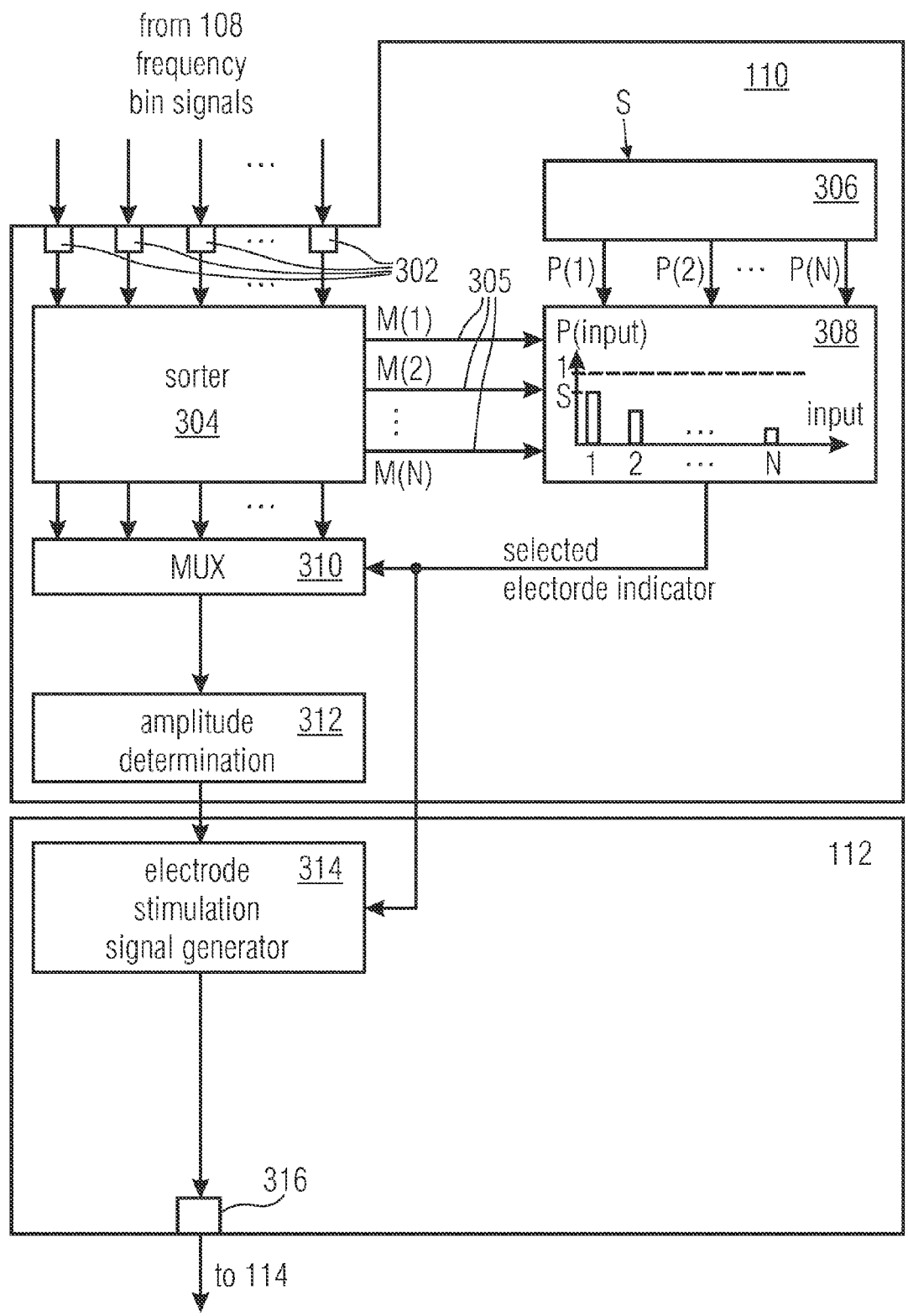
FIG. 3 is a schematic block diagram of components of the neural auditory prosthesis.

A feature extractor and selector module 110 (FES) extracts and/or selects a certain number of the M input samples. Each of the M input samples corresponds to an instantaneous value of one of the plurality of amplitude equalized and loudness-mapped frequency bin signals. Typically, the selected input samples exhibit properties that distinguish them from the remaining input samples. The selected input samples form a set of selected frequency bin signals 305 (FIG. 3). The selection of the set of selected frequency bin signals could change quite frequently, such as once every sample period. Therefore, in terms of a duration of the selected frequency signals, the set of selected frequency bin signals 305 may be as short as a single sample. The determination of the set of selected frequency bin signals 305 may be based on various criteria, such as a magnitude of the input samples. The set of selected frequency bin signals comprises N selected frequency bin signals. These N selected frequency bin signals or samples typically have the largest magnitudes, and they are sorted so that a first selected frequency bin signal M(1) represents the highest amplitude and M(N) the n-th highest amplitude sample, i.e. the frequency bin signal with the lowest magnitude of the selected frequency bin signals. In the exemplary implementation mentioned above, the number N of selected frequency bin signals in the set of selected frequency bin signals is N=3. Typically, the determination of the set of selected frequency bin signals will be based on the magnitude of the input samples to the feature extractor and selector module 110. In this case, the set of selected frequency bin signals may be called a set of strong frequency bin signals, or a set of dominant frequency bin signals. The strong frequency bin signals or the dominant frequency bin signals are those signals that are likely to contain useful information contained in the original sound data that will help the recipient to e.g. understand a word or hear a certain sound. Note that the expression "strong frequency bin signals" does not necessarily mean "strongest frequency bin signals", although it is contemplated that the set of strong frequency bin signals typically contains the frequency bin signals with the N largest magnitudes.

The feature extractor and selector module 110 then selects one frequency bin signal from the set of selected frequency bin signals (or one sample from the set of selected samples). This selection is typically random so that either one of the set of selected frequency bin signals may be selected. The random selection can be biased by means of one or more selection probability values that are assigned to one or more selected frequency bin signals within the selected set. By assigning specific selection probability values to the selected frequency bin signals or samples, the selection of an ultimately retained frequency bin signal/sample for subsequently driving a corresponding electrode of the stimulation device 114 can be controlled in a manner that the sample with the largest magnitude is selected more often than the other samples in the set of selected samples, but not each time. The selection probability values may be chosen as a function of a parameter S which represents the probability of choosing the higher magnitude sample. If S=1.0, then the highest magnitude sample M(1) will be selected in each cycle, hence, the stimulation is deterministic. If, for example, S=0.8 and N=3, then the probability of selecting M(1), MJ(2) or M(3) is 80%, 16% and 4%, respectively. If S<1.0, then the stimulation is stochastic, which may account for a better bio-compatibility. In the above mentioned exemplary implementation, the parameter S was chosen to be S=0.9.

A stimulus builder module 112 (SBM) determines other properties (like pulse type, pulse width, etc.) of the stimulus signal based on the properties of the used stimulation device and on the patient's preferences. The stimulus builder module 112 also receives data from the feature extractor and selector module 110, in particular which one of the set of selected frequency bin signals has been selected by means of the random selection process. The selection of a certain frequency bin signal/sample determines which electrode of the stimulation device 114 will be activated. The feature extractor and selector module 110 may also provide data regarding a magnitude of the selected sample to the stimulus builder module 112.

To reduce recurrence in stimulation, it may be useful to stochastically change one or more stimulus parameter(s) over time. One possible waveform for an electrode stimulation signal may be a biphasic pulse which has a short gap (approximately 8 μs) between the two phases. The duration of the gap may be subjected to random variations that can also be observed with persons having normal hearing. Such random variations reflect natural processes and are believed to improve perception capabilities of the recipient of the neural auditory prosthesis 100. In the exemplary implementation mentioned above, the phase gap G is randomly varied among subsequent stimulations in the range of $[(1-J) \cdot G, (1+J) \cdot G]$, where J=0.1. Typically, J will be in the interval [0, 1], but closer to 0 than to 1 ($0 \leq J \ll 1$).

In summary, the neural auditory prosthesis 100 shown in FIG. 1 receives a sound signal, analyzes the sound signal with respect to its frequency contents in a number of frequency bands, normalizes the obtained frequency bin signals, selects a reduced number of the frequency bin signals, randomly selects a single one of the frequency bin signals, and generates an electrode stimulation signal based on parameters and properties of the selected frequency bin signal. Finally, the electrode stimulation signal is applied to an electrode corresponding to a frequency band of the selected frequency bin signal.

Some of the above mentioned signal processing blocks or tasks may be omitted. For example, the feature extraction and selection module 110 could proceed directly to the random selection of one frequency bin signal without the intermediary step of determining a set of selected frequency bin signals. This may be achieved by assigning very small selection probability values (possibly zero) to those frequency bin signals/samples that have relatively weak magnitudes compared to other frequency bin signals/samples.

Figure 2:
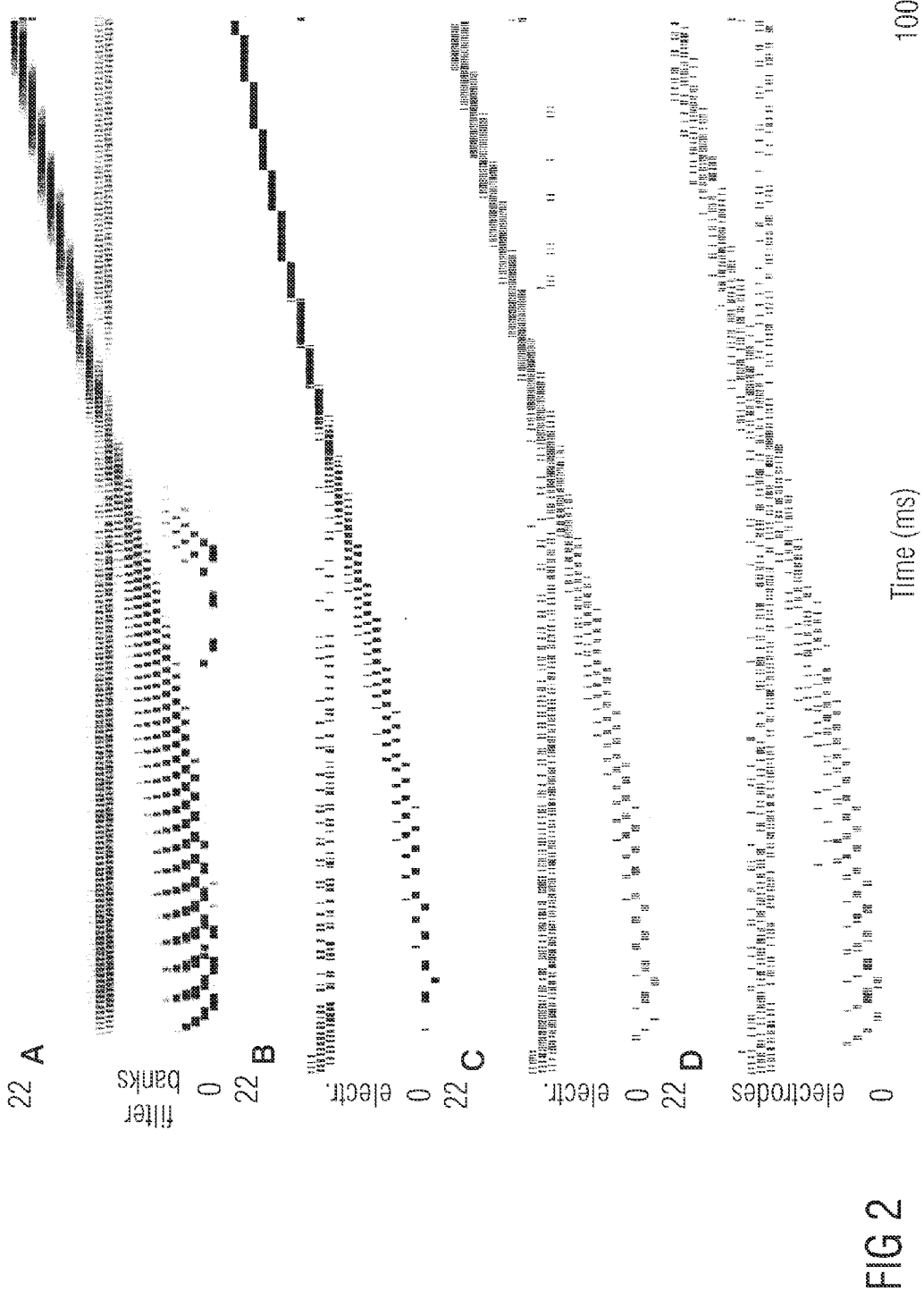
FIG. 2 shows frequency-over-time representations of some signals within the neural auditory prosthesis.

FIG. 2 shows in diagram A the output of the filter bank 104 over time for a synthetic input sound consisting of a sine sweep signal (275 Hz to 7750 Hz) and of a constant 2000 Hz pure tone with an amplitude of −6 dB FS relative to that of the sweep. The number of frequency bands M is 22, i.e. already reduced to match the number electrodes of the stimulation device 114. The diagram of FIG. 2A illustrates a magnitude of a frequency bin signal within a certain frequency band at a certain instant in time as different shades of gray. The total sample rate TSR is TSR=9000/s. It can be seen that the 2000 Hz pure tone shows up on three different frequency bands. Furthermore, a low frequency beat can be observed where the sine sweep signal approaches a frequency of 2000 Hz of the constant 2000 Hz pure tone.

The diagram B in FIG. 2 shows an output of the feature of the feature extractor selector module 110 generated on the basis of the filter bank output shown in diagram A of FIG. 2. The feature extractor and selector module output of diagram B was obtained by configuring the signal processing with the following parameters: The repetition penalty P was chosen to be 0.0 dB, i.e. a current frequency bin signal or sample was not attenuated if it was used for generating the electrode stimulation signal in the previous cycle. The parameter S controlling the distribution of selection probability values among the plurality of frequency bin signals 105 was set to S=1.0. This means that the selection of the frequency bin signal to be used for the generation of the actual stimulation signal is deterministic. Hence, the feature extractor and selector module 110 selects the frequency bin signal having the highest magnitude.

The diagrams C and D in FIG. 2 show further outputs of the frequency extractor and selector module 110 obtained under different parameter settings. The filter extractor and selector module output shown in diagram C was obtained by setting the repetition penalty attenuation to P=10.0 dB and the parameter S controlling the distribution of the selection probability values to S=1.0 (deterministic). In the case of diagram D, the repetition penalty attenuation was set to P=10.0 dB and the parameter S was set to S=0.5 (stochastic). Especially in the case of diagram D it can be seen that the chosen parameter settings allow the softer pure tone to show up steadily in the stimulation pattern. In contrast, the softer pure tone vanished completely in the second half of the sine sweep signal for the parameter settings corresponding to the feature extractor and selector module output shown in diagram B. The parameter settings valid for diagram C (repetition penalty attenuation and deterministic frequency bin signal selection) shows some improvement. Introducing a certain degree of randomness, as has been done for the generation of the feature extractor and selector module output shown in diagram D, yields a stimulation pattern that reflects a major part of the relevant information contained in the original input sound. The diagrams A to D of FIG. 2 cover a time span of 100 ms.

The presented method of electrode stimulation allows for keeping a large portion of fine temporal structure of an original signal when applied to the output of the filter bank 104. Among other possible effects, cochlear pressure waves, also called delay trajectories, remain part of the stimulation pattern, which is believed to increase speech perception in patients. For the same reason, phase-locking, compression and adaptation effects of the (simulated) basilar membrane and inner hair cell complex can be relatively faithfully represented, which leads to better pitch and onset perception.

The presented system does not inherently depend on block-by-block processing, neither on the audio input side, nor on the stimulation output side. An effective lag between two identical devices in a binaural setup using this system would be 1/TSR seconds at maximum, if the processing blocks are capable of processing data belonging to one sample period in a substantially immediate manner. Some filter bank technologies currently in use, such as fast Fourier transformation (FFT) may relay on several sample periods for analyzing an input signal with respect to the input signal's frequency content, which introduces a delay to the signal processing. In this case, the effective lag between two identical devices in a binaural setup is somewhat random and could be as long as the introduced delay, i.e. several sampling periods or even tens of sampling periods. With the immediate signal processing made possible by the teachings disclosed herein, horizontal-plane localization of sound sources is possible to a degree not achieved by most currently available systems.

Horizontal-plane localization ability with binaural systems may further be improved by stochastically varying the phase gap in the stimulus builder module 112 as will be explained in connection with the description of FIG. 7.

The inclusion of stochastic processing in the signal processing within the feature extractor and selector module 110 and/or the stimulus builder module 112 are expected to increase bio-compatibility and overall perception quality.

FIG. 3 shows a schematic block diagram of the feature extractor and selector module 110 and the stimulus builder module 112. The feature extractor and selector 110 receives a plurality of frequency bin signals 105 from the loudness mapping function 108. It is however possible that the plurality of frequency bin signals 105 is provided by the filter bank 104 or the amplitude equalizer 106, i.e. the neural auditory prosthesis 100 does not comprise a loudness mapping function 108. The plurality of frequency bin signals 105 arrive at a plurality of signal inputs 302. Within the feature extractor and selector module 110 the plurality of frequency bin signals are forwarded to a sorter 304 that is adapted to determine a ranking of the plurality of frequency bin signals 105 with respect to a certain criterion, such as a magnitude. The frequency bin signals 105 are processed in a piecewise manner, that is the sorter 304 analyzes pieces of the frequency bin signals that fall within a certain time span, for example one sample period.

Information about an order of the plurality of frequency bin signals determined by the sorter 304, or the frequency bin signals arranged in the determined order themselves, or a part of the plurality of frequency bin signals such as those having the largest magnitudes, is output by the sorter 304 and provided to a random selector 308. The random selector 308 selects one frequency bin signal from the ordered set of frequency bin signals, for example, according to a random process which is controlled by one or more selection probability values. Typically, a relatively high selection probability value is assigned to the frequency bin signal having the largest magnitude. A smaller selection probability value will be assigned to the frequency bin signal having the second largest magnitude, and so on. In FIG. 3 it is assumed that the sorter 304 provides a set of frequency bin signals, or of references to the frequency bin signals, which has N elements. As such, the sorter 304 may comprise a selector adapted to select a reduced set of selected frequency bin signals 305 that has fewer than the plurality of frequency bin signals. A size of N=3 for the reduced set of selected frequency bin signals provides the random selector 308 with the three frequency bin signals having the three largest magnitudes from which the random selector 308 is adapted to pick one by means of a random process taking into account the selection probability value(s).

The selection probability values are referenced in FIG. 3 with $p(1)$, $p(2)$, and $p(N)$. The selection probability values are provided to the random selector 308 by a selection probability value assigner 306 that sets the selection probability values $p(1)$ for the frequency bin signal having the largest magnitude, the selection probability value $p(2)$ for the frequency bin signal having the second largest magnitude, and also the selection probability value $p(N)$ for the frequency bin signal having the n'th largest magnitude and which typically is the last one considered in the set of selected frequency bin signals. The selection probability value assigner 306 may take a parameter S as an input and the selection probability values are calculated as a function of the parameter S.

An output of the random selection 308 is either an indicator for an electrode selected by the random selector 308 or a selected frequency bin signal. In the former case, the selected electrode indicator is provided to a multiplexer 310 as a control signal. The multiplexer 310 comprises a plurality of inputs for the plurality of frequency bin signals 105. In FIG. 3 the plurality of frequency bin signals is passed onto the multiplexer 310 from the sorter 304, but this is only one of several possible implementations. For example, the multiplexer 310 could be connected directly to the signal inputs 302. The multiplexer 310 connects one of its inputs corresponding to the selected electrode indicator with an output of the multiplexer 310. Thus, the selected frequency bin signal is passed onto an amplitude determination module 312. An alternative to providing the multiplexer 310 could be to include the multiplexer capability in the random selector 308. A random selector 308 would then receive the selected frequency bin signals and forwards one frequency bin signal of the set of selected frequency bin signals to the amplitude determination module.

The amplitude determination module 312 analyzes the selected frequency bin signal with respect to an amplitude thereof. Typically, an amplitude determination is already performed by the sorter 304 so that the amplitude determination module 312 may simply access or use the corresponding amplitude data provided by the sorter 304. The amplitude determination module 312 produces a parameter or a parameter set that is used by an electrode stimulation signal generator 314 which is a part of the stimulus builder module 112. The electrode stimulation signal generator is adapted to create an electrode stimulation signal based on the parameter(s) provided by the amplitude determination module 312 and/or the feature extractor and selector module 110. The generation may use a template for the electrode stimulation signal which is adjusted according to the provided parameter(s). The generated electrode stimulation signal is provided to an electrode stimulation signal output 316 of the stimulus builder module 112 from where it is passed on to the stimulation device 114. The electrode stimulation signal generator 314 also receives the selected electrode indicator from the random selector 308 so that the generated electrode stimulation signal may comprise an information about the selected electrode to which the electrode stimulation signal shall be applied. Although only a single electrode stimulation signal output 316 is shown in FIG. 3, the electrode stimulation signal generator 314 and the stimulus builder module 112 could comprise a plurality of electrode stimulation signal outputs, for example one output per electrode of the stimulation device 114.

The proposed feature extractor and selector module 110 introduces a degree of randomness in the electrode selection which reflects phenomena that can be observed in the auditory sense of persons who are not hearing impaired. Since this is a natural phenomenon, the healthy remainder of the auditory sense of the recipient of the neural auditory prosthesis 100 possibly reacts better to a slightly random signal than to a completely deterministic signal.

Figure 4A:
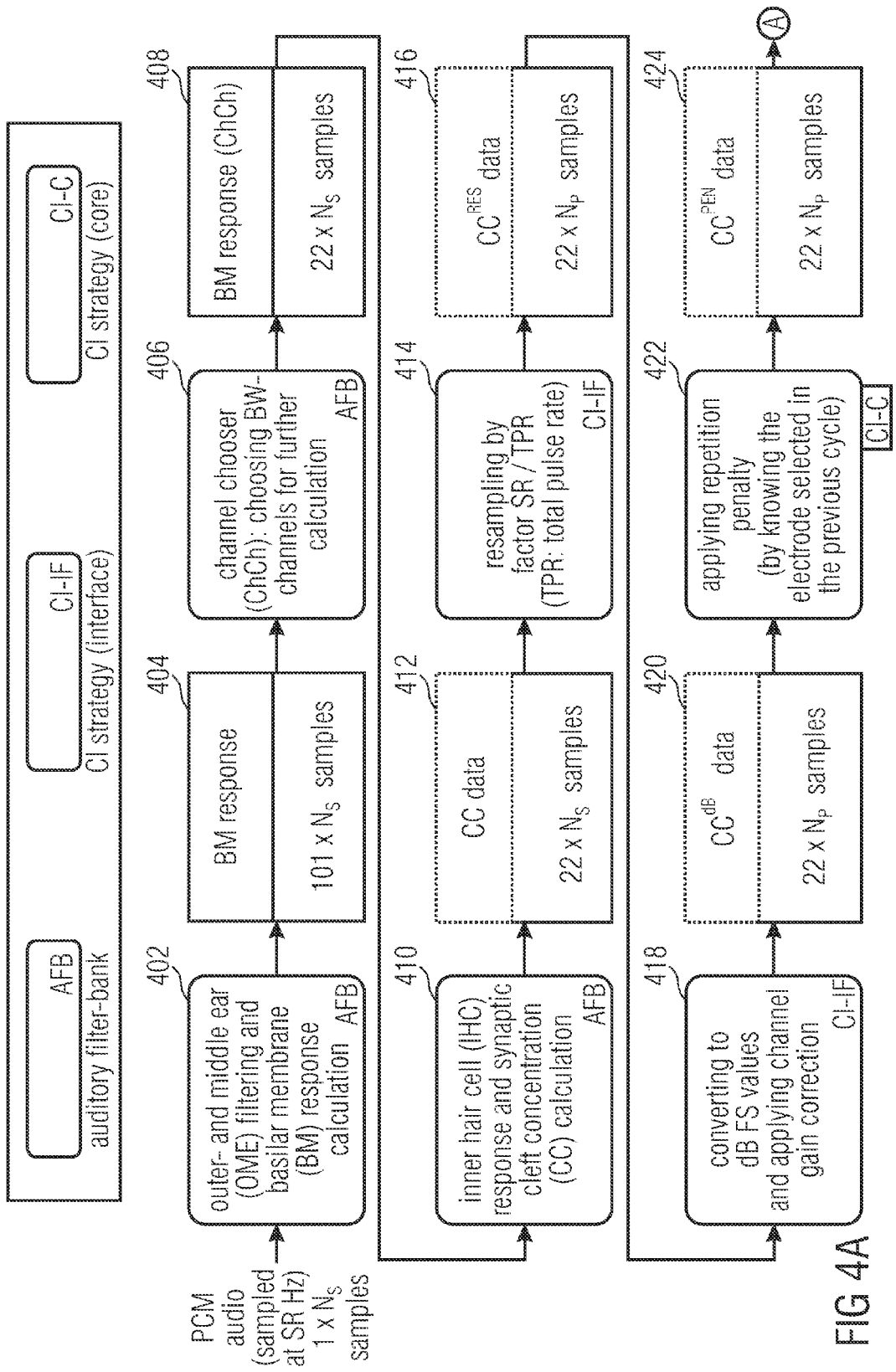
FIGS. 4A and 4B show a schematic flow chart of a method according to the teachings disclosed herein.
Figure 4B:
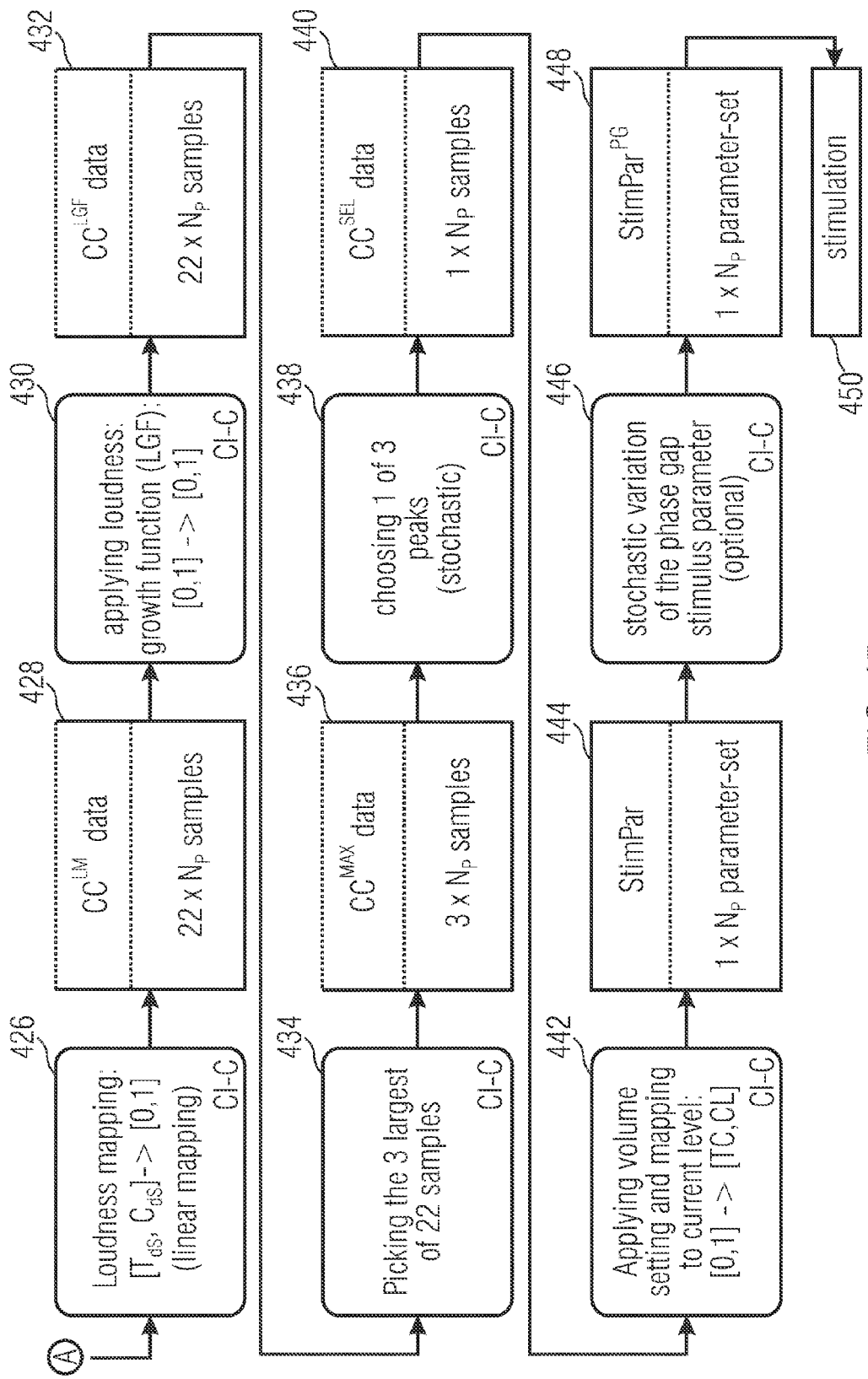

FIGS. 4A and 4B show a schematic flowchart of a method for generating a control signal for a neural auditory prosthesis 100. The method starts by receiving a pulse code modulated (PCM) audio signal that has been sampled at a sample rate SR, e.g. 44.1 KHz. Often, the sampling rate SR of the audio signal is higher than a pulse rate of the electrode stimulation signal at the output of the neural auditory prosthesis 100. Therefore, a number of $N_s$ samples of the audio signal can be processed during one stimulation cycle. In a neural auditory prosthesis 100 in which the method or the device according to the teachings disclosed herein is implemented, the PCM audio signal is typically provided by components of the neural auditory prosthesis 100 not depicted in FIG. 3, such as a microphone, an amplifier, and an analog-to-digital converter.

A first action of the method illustrated in FIG. 4A is to perform outer and middle ear (OME) filtering, as shown in block 402. A basilar membrane (BM) response calculation is also performed at 402. The basilar membrane response is a plurality of frequency-filtered signals obtained by processing the PCM audio signal by means of a simulation model of the basilar membrane. In a simplified manner, the simulation model of the basilar membrane can be regarded as a filter bank comprising a plurality of bandpass filters that are closely spaced in the frequency domain. Block 404 represents the basilar membrane response which comprises 101 frequency bin signals having $N_s$ samples each. The number of 101 frequency bin signals is purely exemplary.

At 406 some of the frequency bin signals from the basilar membrane response 404 are chosen for further calculation: This action or functional block 406 is called channel chooser (ChCh). In the exemplary implementation shown in FIG. 4A normally 22 frequency bin signals out of the original 101 frequency bin signals are kept, as can be seen at block 408 representing the basilar membrane response after channel choosing ("BM response (ChCh)"). The basilar membrane response after channel choosing 408 thus comprises 22 frequency bin signals with a length of $N_s$ samples each in the exemplary implementation of FIG. 4A.

The choice of the channels at 406 is typically made by comparing characteristic frequencies (CF) of the channels (e.g. a center frequency of the corresponding frequency bin) with characteristic frequencies of the electrodes in the stimulation device 114. For example, the channels may be selected so that their center frequencies are closest to the center frequencies used in an advanced combination encoder (ACE) strategy of a given recipient of the neural auditory prosthesis 100.

At 410 the data on the chosen channels will first be processed by simulated inner hair cells tuned to act as high-spontaneous rate (HSR) inner hair cells. The high-spontaneous rate inner hair cells start to operate at hearing threshold level and saturate at about 65 dB SPL. This simulation stage is followed by a synaptic cleft model so that the output of the auditory model can be thought of as a neurotransmitter concentration in the synaptic cleft (denoted as CC data in FIG. 4A at reference sign 412) at given positions along the basilar membrane. A CC data 412 corresponds to the output of the filter bank 104 and thus the plurality of frequency bin signals 105. The filter bank output is interfaced to a core strategy module.

As a first action of the interfacing, the filter bank output 412 is resampled in time, at 414 to match the total stimulation rate (also denoted as total pulse rate: TPR). This results in a data set $CC^{RES}$ data 416 comprising the 22 resampled frequency bin signals having $N_P$ samples each. The value $N_P$ may be equal to 1 so that each frequency bin signal in the data set 416 comprises a single (instantaneous) sample only. At 418, data elements of the resampled filter bank output 416 related to channels not marked as inactive are converted to dB FS units. This is possible, since the $CC^{RES}$ values are non-negative (zero elements and values related to inactive channels will be translated to −99.9 dB FS values to avoid log domain error). The channel gain correction can also be applied, if necessitated, via simple addition to change the perceived loudness per channel.

In an exemplary implementation of the method of generating a control signal for a neural auditory prosthesis 100 all further processing steps may be reside in a loop on a sample-by-sample basis (or on a stimulation-cycle basis), so that an operation of a current cycle may use the results from a previous cycle.

Starting with the data set 420 of frequency bin signals converted to dB FS values, a repetition penalty 422 is applied to that channel of the data set 420, which was involved in a stimulation of the corresponding electrode in the last cycle, or in at least one of the last cycles. By increasing the value of the repetition penalty, the probability of a repeated selection of the same electrode in consecutive cycles can be decreased or even completely disallowed. Applying the repetition penalty at 422 produces a data set 424 ($CC^{PEN}$ data).

The method continues in FIG. 4B as indicated by the connector A. At 426 a loudness mapping is performed. In the exemplary implementation illustrated in FIGS. 4A and 4B the values in each channel of the data set 424 are analyzed and mapped from a loudness range to a normalized range. A lower limit of the loudness range is provided by a threshold level and a higher limit of the loudness range is given by a comfort level. Typically, the threshold levels and the comfort levels are different for the chosen channels. The threshold level is mapped to the value 0.0 of the normalized range and the comfort level is mapped to the value 1.0 of the normalized range. Values between the threshold level and the comfort level are mapped to values within the normalized range [0.0, 1.0]. The mapping may be linear or non-linear, e.g. according to a square law, an exponential law, a logarithmic law, or a sigmoid law. Values smaller than the threshold level are mapped to 0.0, while values larger than the comfort level are mapped to 1.0. The data set containing the loudness mapped frequency bin signals is designated by the reference sign 428 in FIG. 4B.

Next, a loudness growth function (LGF) is applied to the loudness mapped data 428 ($CC^{LM}$ data), at block 430. The loudness growth function maps the normalized range [0, 1] to another normalized range [0, 1] by means of a curve that is individual for each channel of the neural auditory prosthesis 100. The curves of the plurality of loudness growth functions for the plurality of chosen frequency bin signals is controlled by a curve shaping factor which is allowed to vary among the channels. While in theory it would be possible to combine the loudness mapping 426 and the loudness growth function 430, their separation may be easier to handle for an audiologist when adjusting the neural auditory prosthesis 100 to a specific recipient. A block 432 represents the data of the chosen channels after the loudness growth function ($CC^{LGF}$ data).

In the next step, the three channels having the largest amplitude values in the data set 432 are searched for. The determined maximum values are sorted in descending order and are stored along with their original (channel) indices in a data structure $CC^{MAX}$. A first data element $CC^{MAX}[0]$ of the data structure $CC^{MAX}$ 436 represents the largest maximum, $CC^{MAX}[1]$ the second largest maximum and $CC^{MAX}[2]$ the third largest maximum. The number of three maximum values is exemplary. For the purposes of the method disclosed herein, any number of determined maximum values equal to or larger than two may be used. It can happen that all chosen channels have signal values in the data set 432 that are below a processing threshold. In this case, a null stimulation will be scheduled for the current cycle and all consecutive processing steps are skipped.

If not only the largest maximum $CC^{MAX}[0]$ was found, but also the second largest maximum $CC^{MAX}[1]$ and possibly further largest maximums according to the order determined by the processing block 434, then the next task is to select one of them. Based on the settings controlling a randomness of the selection process, such as the parameter S (FIG. 3), this selection can be deterministic or stochastic. The parameter S represents the probability of choosing the largest maximum. If S=1.0, then in each cycle the largest maximum $CC^{MAX}[0]$ will be selected and the stimulation is deterministic. If S<1.0, then the stimulation is stochastic, which may account for better bio-compatibility. The application of the parameter S may be recursive, that is in a first recursion the selection probability values p(1) for the largest maximum is determined and by calculating 1−p(1) the combined probability for the second largest maximum to the n'th largest maximum is calculated. In a subsequent recursion, the selection probability value for the second largest maximum p(2) is determined by calculating (1−S). If, for example, three peaks were found and S=0.8, then the selection probability values p(1), p(2), and p(3) of selecting $CC^{MAX}[1]$, $CC^{MAX}[2]$ or $CC^{MAX}[3]$ is 80%, 16% and 4%, respectively. The action of choosing one of three peaks is represented by block 438 in FIG. 4B. Block 440 represents the selected data element $CC^{SEL}$ containing $1 \times N_p$ samples.

At block 424 a volume setting is performed on the selected frequency bin signal or sample. The volume setting comprises adjusting a dynamic range determined by the difference of the threshold and comfort levels of the electrical stimulation. If no custom volume is specified, then a default setting for the volume is used. In the same processing step the volume-adjusted values are mapped to a current level range of [threshold current level, comfort current level] and rounded to "current level" integers. Furthermore, stimulation parameters are gathered to form a stimulus parameter set (denoted as StimPar data in FIG. 4B, reference sign 444). The stimulation parameters may be a width of the electrode stimulation signal (e.g., a duration of a gap occurring during the electrode stimulation signal) and an indicator of the electrode to which the electrode stimulation signal shall be applied. The indicator of the electrode to be used for stimulation can typically be taken from the data set 440.

At the optional block 446 a possibility is given for stochastically varying different ones of the parameters controlling the generation of the electrode stimulation signal. As an example, the possibility may be given to vary the phase gap length property of a biphasic electrode stimulation signal between well-defined limits in a stochastic manner. This random variation adds some irregularity to the stimulation signal, which reduces periodic characteristics, while preserving fine temporal structures of the original signal. For example, a phase gap variation AG may be introduced which causes a length of the phase gap to be varied among subsequent stimulation cycles in a range of $[(1-\Delta G) \cdot G_0, (1+\Delta G) \cdot G_0]$. The variable $G_0$ represents an average length of the phase gap. The phase gap variation AG is in the range [0, 1] and typically has a value much smaller than 1, e.g. $\Delta G=0.1$. The application of such a phase gap variation may be subjected to a compatibility with a current stimulation mode (determined e.g. by the stimulation rate). In particular, it may be that the current stimulation mode allows certain maximal values for the phase gap variation. In case the application of a phase gap variation or of the value of the phase gap variation is not compatible with the current stimulation mode the action 446 may be completely skipped.

Whether or not a stochastic variation of one or more stimulus parameters has been performed, a corresponding parameter set 448 is provided. The stimulation parameter set 448 is then used to generate and apply a corresponding electrode stimulation signal at block 450.

Exemplary configuration parameters related to the auditory filter bank 104 are listed in the following table:

| Configuration Key | Exemplary values | Comment |
| --- | --- | --- |
| SFREQ | 44100.0 | Sampling frequency (in Hz). |
| BM_NO_SECTIONS | 101 | Number of BM-sections to be simulated. |
| BM_MAX_LAT_COUPL | 8 | Number of laterally coupled sections. |
| BM_MAX_BARK | 25 | Max frequency that the BM should simulate (in Bark). |
| BM_DELTA_Z | 0.25 | Frequency spacing of adjacent BM-sections (in Bark). |
| BM_BM_PREAMP | −50.0 | BM input and output range amplification (in dB). They |
| BM_FACTOR | −113.0 | account for the right working range of the BM. |
| BM_NO_OME | 0 | Whether to disable outer and middle ear filtering. |
| BM_HWM_CQNU_FACTOR | 0.6 | Factors to fine-tune the delay trajectory Shapes. |
| BM_HWM_C_FACTOR | 3.0 | |
| BM_USAT_FACTOR1 | 5.0 | Factors to fine-tune the non-linear amplitude |
| BM_USAT_FACTOR2 | 200.0 | characteristics of the BM model. |
| BM_REAL_CFS | 84.9, 97.0, . . . , 19077.7 | Estimated channel frequencies at 55.0 dB SPL. |
| POST_BM_CHANNELS | 22 | Number of sections the channel chooser should keep. |

-continued

| Configuration Key | Exemplary values | Comment |
| --- | --- | --- |
| BM_CHANNEL_MAP | 11, 16, . . . , 86 | Sections to keep by channel chooser. |
| C_CILIA | −55.0 | Coupling factor: IHC release probability to cleft (in dB). |
| KT_FACTOR | 5.69 | Cleft concentration amplification factor. |

Exemplary parameters relative to the operation of the amplitude equalizer 106, the loudness mapping function 108, the feature extractor and selector module 110, and the stimulus builder module 112 are listed in the following table:

| Configuration Key | Exemplary values | Comment |
| --- | --- | --- |
| MAP_CHANNEL_AC | 1, 1, 1, 1, 1, 1, 1, . . . , 1 | Flag active channels (1: active, 0: inactive). |
| MAP_CHANNEL_TL | 0, 0, 0, 0, 0, 0, 0, . . . , 0 | Threshold/comfort level per channel (in Current |
| MAP_CHANNEL_CL | 255, 255, 255, . . . , 255 | Level), as in the personalized MAP of the Cl-user. |
| MAP_CHANNEL_GAIN | 0.0, 0.0, 0.0, . . . , 0.0 | Gain correction per channel (in dB). |
| MAP_CHANNEL_TDB | −37.6, −38.8, . . . , −67.0 | $CC^{dB}$ data levels for a pure tone of the respective |
| MAP_CHANNEL_CDB | −20.4, −22.5, . . . , −33.7 | center frequency with T-SPL/C-SPL loudness. |
| MAP_CHANNEL_CSF | 0.01, 0.01, . . . , 0.01 | Curve shaping factors for loudness mapping. |
| MAP_TOT_PULSRATE | 9000 | Total pulse rate (in 1/s). |
| MAP_PHASE_WIDTH | 25.0 | Phase width (in µs). |
| MAP_PHASE_GAP | 8.0 | Inter-phase gap (in µs). |
| MAP_REF_ELECTRODE | −3 | Reference electrode (−3, −2 or −1). |
| MAP_GAP_JITTER | 0.1 | Inter-phase gap jitter (1.0: max, 0.0: none). |
| MAP_MAX_RANDOMNESS | 0.1 | Level of randomness in maxima selection (0.5: max). |
| MAP_REP_PENALTY | 10.0 | Level with which a filter-bank band should be attenuated if already stimulated in the last cycle (in dB). |
| MAP_DEFAULT_VOLUME | 1.0 | Default volume in stimulation (1.0: max, 0.0: min). |

Figure 5:
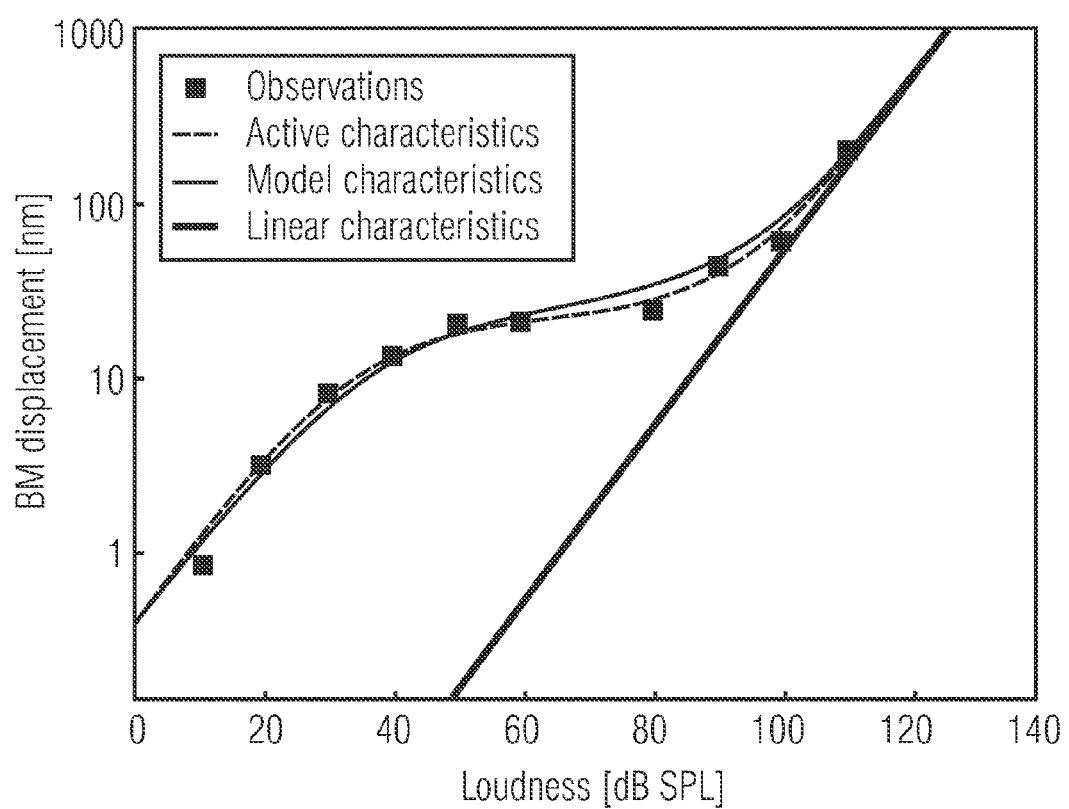
FIG. 5 is a graph illustrating a characteristic of a basilar membrane as a function of loudness.

FIG. 5 shows a response of a basilar membrane and of a model thereof for a 1000 Hz pure tone at various loudness levels. The observations obtained from the original basilar membrane are represented as black squares in FIG. 5 and show that the basilar membrane has a relatively high sensitivity for loudness differences in a low loudness range, as well as in a high loudness range. In an intermediate loudness range between approximately 40 dB SPL and 80 dB SPL the curve is relatively flat, indicating that the basilar membrane has a relatively low sensitivity towards loudness in this range. A simple linear model of the basilar membrane behavior is shown in FIG. 5 as a thick full line that asymptotically approaches the observation at high loudness levels. The linear model substantially neglects a basilar membrane response for loudness levels below approximately 60 dB SPL. A model characteristics represented by a thin full line in FIG. 5 follows the observations more closely, while the active characteristics drawn as a thick dashed line are still closer to the observations. A basilar membrane input and output range amplification and the factors for fine-tuning the amplitude characteristics may be tuned in a way that the non-linear characteristic of the simulated basilar membrane best fit experimental data.

Figure 6:
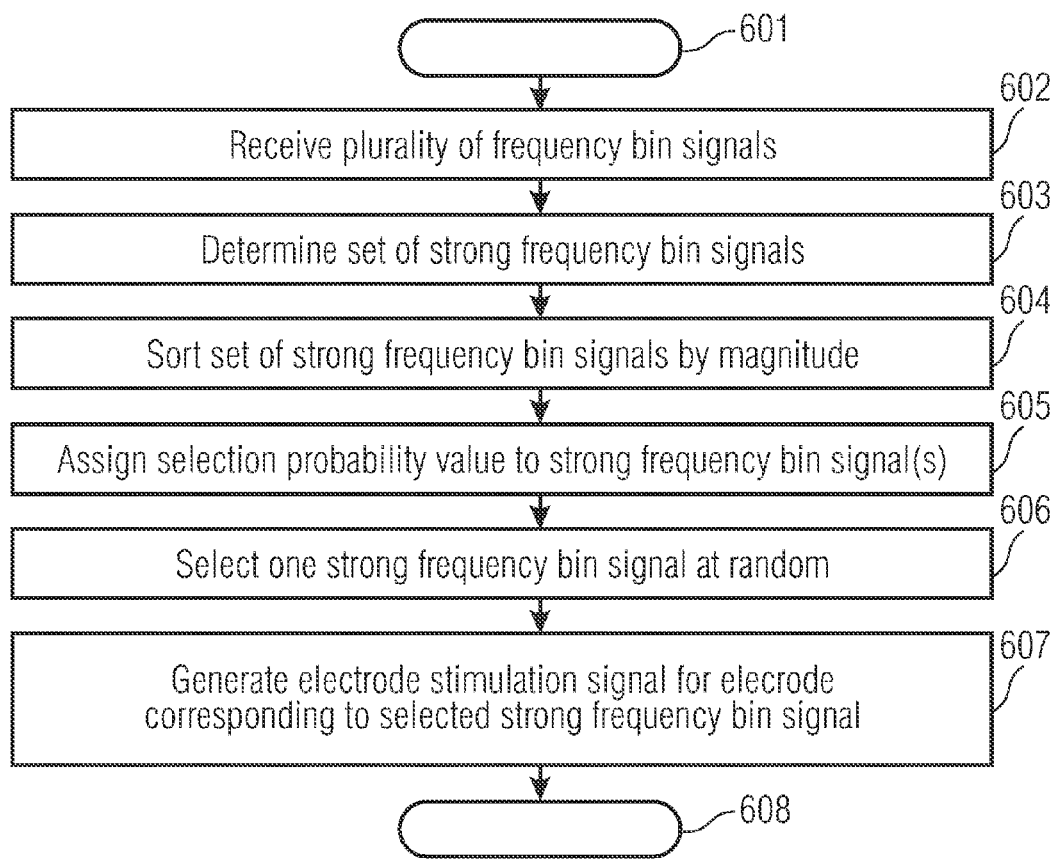
FIG. 6 is a schematic flowchart of the method according to the teachings disclosed herein.

FIG. 6 shows an exemplary, schematic flowchart of a method according to one aspect of the teachings disclosed herein. After a start of the method at 601 a plurality of frequency bin signals is received at 602. The plurality of frequency bin signals may correspond to the electrodes available in a stimulation device 114 of an auditory prosthesis 100. At an optional action 603 a set of strong frequency bin signals is determined. A frequency bin signal may qualify as "strong" if it fulfills one or more criteria, such as having a large magnitude.

At another optional action 604 the set of strong frequency bin signals is sorted according to magnitude so that a frequency bin signal having the largest magnitude, a frequency bin signal having the second largest magnitude, and so on, can be determined.

At least one selection probability value is assigned to at least one of the strong frequency bin signals at 605. Typically, the selection probability value is assigned to all of the strong frequency bin signals in the selected set of strong frequency bin signals. At an action 606 one of the strong frequency bin signals is selected by means of a random process that is "biased" by the selection probability value(s) assigned to the strong frequency bin signals at the previous action 605. Typically, the frequency bin signal having the largest magnitude will be selected with a higher probability than the frequency bin signal with the second largest magnitude, and so on. It is, however, possible that the second largest frequency bin signal or even lower ranking frequency bin signals, in terms of their magnitude, are selected during the action 606 if their assigned selection probability value is non-zero.

The electrode stimulation signal is then generated at 607 for an electrode that corresponds to an index of the selected strong frequency bin signal. The method ends at 608. The method is typically repeated once per stimulation cycle.

Figure 7:
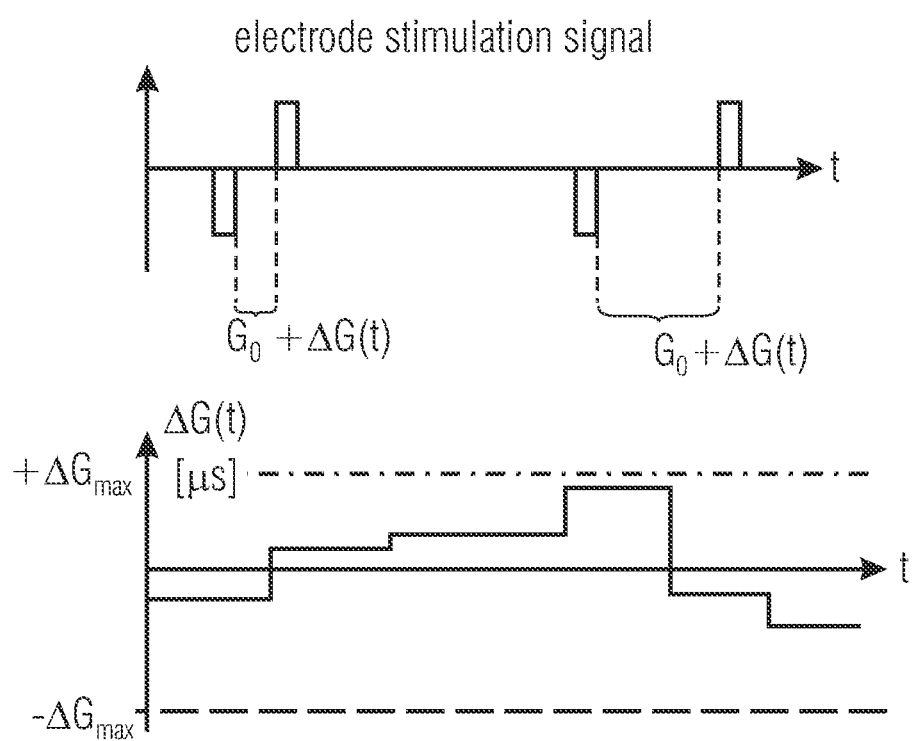
FIG. 7 shows two temporal diagrams illustrating an aspect of stochastic generation of stimulation signals according to an aspect of the teachings disclosed herein.

FIG. 7 illustrates another option for introducing a degree of randomness to the generation of the electrode stimulation signal. The upper diagram in FIG. 7 shows a wave form of two consecutive biphasic stimulation pulses. Each of the two biphasic stimulation pulses begins with a negative pulse followed by a gap G. After the gap G a positive pulse follows. A duration of the gap G is given by $G_0+\Delta G(t)$, where $G_0$ is an average duration of the gap G and the term $\Delta G(t)$ is a time-varying, random portion of the gap duration. Thus, the two consecutive biphasic pulses of the electrode stimulation signal may have different gap durations.

The lower diagram of FIG. 7 shows a waveform illustrating the temporal evolution of the time-variable, random portion $\Delta G(t)$, measured in microseconds. A new value for $\Delta G(t)$ is determined in a periodical, random manner. For the sake of illustration, several random determinations are shown in the lower diagram of FIG. 7, even though one random determination per stimulation cycle may be sufficient. The time-variable, random portion $\Delta G(t)$ of the gap duration may assume any value between two limits $-\Delta G_{max}$ and $+\Delta G_{min}$.

The probability density distribution may be suitably chosen, such as a uniform distribution or a Gaussian distribution.

The randomly determined duration of the phase gap may be used in block 446 of FIG. 4B.

Figure 8:
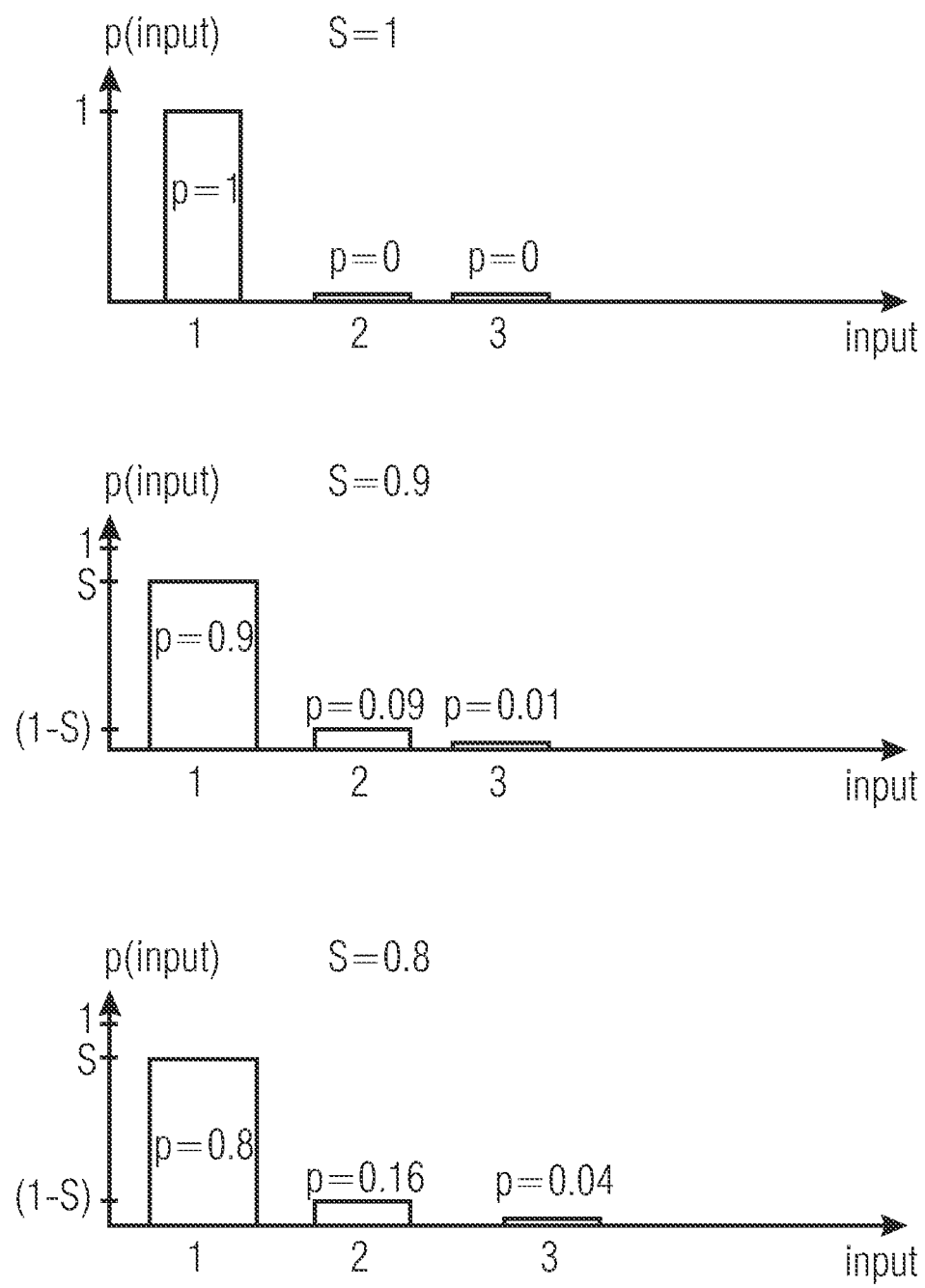
FIG. 8 shows three exemplary probability density distributions illustrating stochastic electrode selection according to an aspect of the teachings disclosed herein.

In FIG. 8 three different probability distribution densities are shown for the random process of selecting one frequency bin signal, and consequently, a corresponding electrode via which the electrode stimulation signal of the current stimulation cycle will be applied. In the upper diagram of FIG. 8, the parameter S has been chosen to be S=1. This means that the probability of selecting the largest magnitude frequency bin signal p(1) is equal to 1, e.g. 100%. The selection probability values for the remaining frequency bin signals in the set of strong frequency bin signals is p(2)=p(3)=0. This means that the randomness in the frequency bin signal selection process has been eliminated and that the frequency bin signal selection is in fact deterministic.

In the middle diagram of FIG. 8 the parameter S has the value 0.9. This leads to the following selection probability values: p(1)=0.9; p(2)=0.09; and p(3)=0.01. In the lower diagram the parameter S is equal to 0.8. The resulting selection probability values are p(1)=0.8; p(2)=0.16; and p(3)=0.04.

Figure 9:
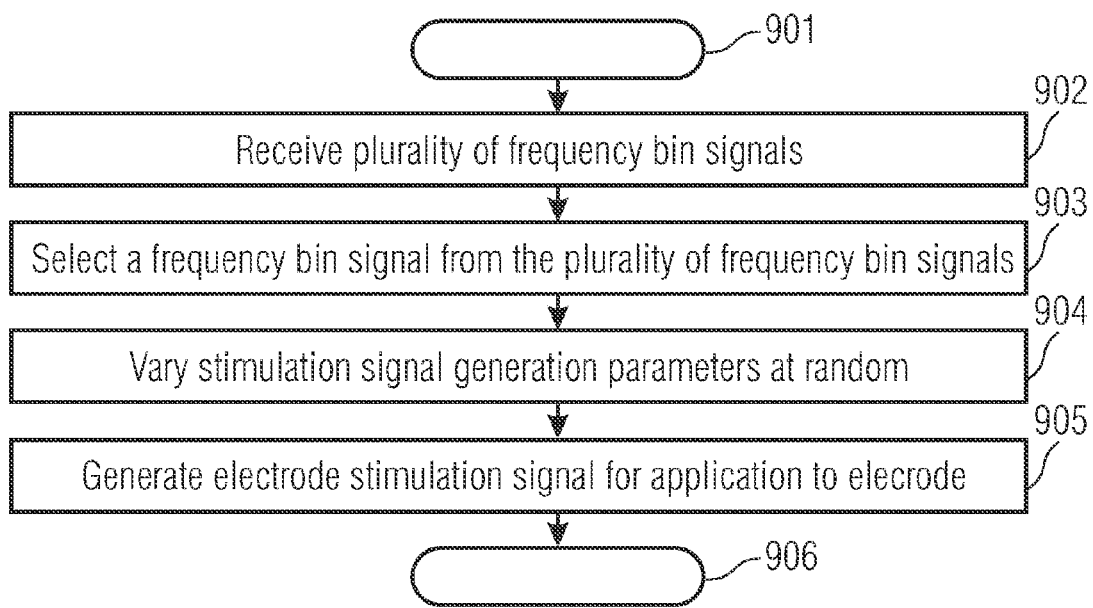
FIG. 9 shows a schematic flowchart of an aspect according to the teachings disclosed herein.

FIG. 9 shows a schematic flow diagram of a method according to one aspect of introducing a degree of randomness to the generation of an electrode stimulation signal. After the start at 901 a plurality of frequency bin signals is received at 902. At a block 903 a frequency bin signal from the plurality of frequency bin signals is selected. Note that in the context of this aspect of the teachings disclosed herein, none of the frequency bin signals could be selected or several ones of the frequency bin signals could be selected.

At a block 904 the stimulation signal generation parameters used for generating the ultimate electrode stimulation signal is varied at random within predefined bounds. An electrode stimulation signal for application to a corresponding electrode is then generated at 905 according to the stimulation signal generation parameters determined and varied at the action 904. The generated electrode stimulation signal(s) is (are) then applied to the electrode(s) corresponding to the selected frequency bin signal(s). At the block 906 the method ends.

Figure 10:
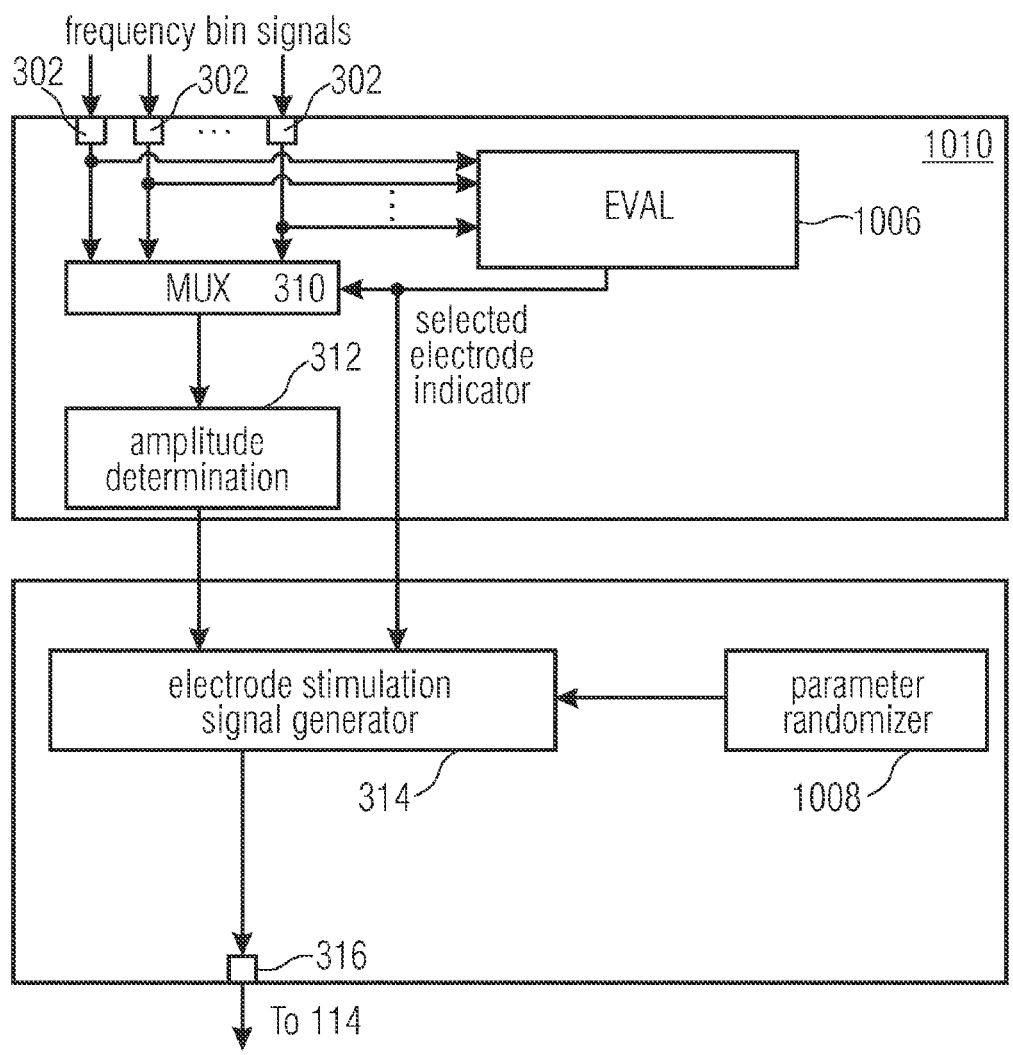
FIG. 10 shows a schematic block diagram of components of a neural auditory prosthesis according to an aspect of the teachings disclosed herein.

FIG. 10 shows a schematic block diagram according to an aspect of the teachings disclosed herein. The plurality of frequency bin signals 105 is received at a plurality of signal inputs 302 from where they are distributed to a multiplexer 310 and an evaluator 1006 which is part of a feature extractor and selector module 1010. The evaluator 1006 may for example implement a selection method for the selective frequency bin signals illustrated and described in the context of FIG. 3. In the alternative, the evaluator 1006 could be implemented according to a deterministic selection scheme. In a manner similar to the one illustrated at FIG. 3, the selected frequency bin signal is forwarded to the amplitude determination 312 where its amplitude is determined.

The stimulus builder module 1012 comprises the electrode stimulation signal generator 314 which receives the determined amplitude value and also an indicator for the selected electrode/frequency bin signal. The stimulus builder module 1012 further comprises a parameter modifier 1008 connected to the electrode stimulation signal generator 314. The parameter modifier 1008 is adapted to provide modified values of stimulation signal generation parameters to the electrode stimulation signal generator 314. The parameter modifier 1008 may comprises a randomizer so that random values of the stimulation signal generation parameters are produced by the parameter modifier 1008. In the alternative, the parameter modifier 1008 may modify the stimulation signal generation parameters in a predetermined manner, thus simulating a random behavior. The electrode stimulation signal generator 314 generates corresponding electrode stimulation signals which are available at an electrode stimulation signal output 316. An example of a stimulation signal generation parameter subject to random variations (within certain bounds) is the duration of the phase gap of a biphasic pulse.

The electrode stimulation signal generator 314 may use predefined templates for the electrode stimulation signals. These templates typically offer a number of options to modify a resulting electrode stimulation signal by adjusting one or more stimulation signal generation parameters.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a digital storage medium, for example a floppy disk, a DVD, a Blue-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine readable carrier.

Other embodiments comprise the computer program for performing one of the methods described herein, stored on a machine readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitionary.

A further embodiment of the inventive method is, therefore, a data stream or a sequence of signals representing the computer program for performing one of the methods described herein. The data stream or the sequence of signals may for example be configured to be transferred via a data communication connection, for example via the Internet.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are performed by any hardware apparatus.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A method of generating a control signal for a neural auditory prosthesis, the method comprising:
   receiving a plurality of frequency bin signals;
   selecting a reduced set of frequency bin signal from the plurality of frequency bin signals depending on magnitudes of the plurality of frequency bin signals, the reduced set of frequency bin signals having fewer frequency bin signals than the plurality of frequency bin signals;
   assigning a selection probability value to each of the reduced set of frequency bin signals depending on each of the reduced set of frequency bin signals, wherein frequency bin signals having relatively higher magnitudes with respect to other frequency bin signals of the reduced set of frequency bin signals are assigned higher-valued selection probability values compared to the selection probability values assigned to frequency bin signals having relatively lower magnitudes;
   selecting one frequency bin signal of the reduced set of frequency bin signals by a random process taking into account the selection probability value assigned to the one frequency bin signal of the reduced set of frequency bin signals;
   varying at least one stimulation signal generation parameter used for generating an electrode stimulation signal and affecting a shape of a basic stimulation pulse, the at least one stimulation signal parameter representing a duration of a phase gap between a positive and a negative pulse of a biphasic pulse, wherein varying the at least one stimulation signal generation parameter is a random process; and
   generating the electrode stimulation signal for application to an electrode of the neural auditory prosthesis corresponding to a frequency of the selected frequency bin signal, the generating of the electrode stimulation signal using the at least one stimulation signal generation parameter subject to variations.

2. The method according to claim 1, wherein the signal generation parameter affects a waveform of the electrode stimulation signal.

3. The method according to claim 2, wherein a template for creating the electrode stimulation signal comprises a temporal gap in which the template is substantially zero-valued between two non-zero sections, and wherein the stimulation signal generation parameter subject to random variation is a duration of the temporal gap.

4. The method according to claim 1, further comprising:
   determining whether one electrode of the neural auditory prosthesis has been selected for stimulation during a previous stimulation cycle; and
   attenuating a corresponding frequency bin signal that corresponds to the determined electrode for stimulation during the previous stimulation cycle.

5. The method according to claim 1, further comprising:
   performing an amplitude equalization on the plurality of frequency bin signals.

6. The method according to claim 1, prior to receiving the selected frequency bin signal, further comprising:
   mapping an amplitude of each one of the plurality of frequency bin signals to a loudness-mapped representation of the amplitude, the mapping being based on patient specific conditions.

7. The method according to claim 1, wherein the plurality of frequency bin signals is received from a filter bank based on a simulation of at least one of a basilar membrane and an inner hair cell.

8. A non-transitory computer readable digital storage medium comprising stored thereon a computer program comprising a program code for performing, when running on a computer, a method for signal processing of a signal in a neural auditory prosthesis, the method comprising:
   receiving a plurality of frequency bin signals;
   selecting a selected frequency bin signal from the plurality of frequency bin signals depending on the magnitudes of the plurality of frequency bin signals, the reduced set of frequency bin signals having fewer frequency bin signals than the plurality of frequency bin signals;
   assigning a selection probability value to each of the reduced set of frequency bin signals depending on each of the reduced set of frequency bin signals, wherein frequency bin signals having relatively higher magnitudes with respect to other frequency bin signals of the reduced set of frequency bin signals are assigned higher-valued selection probability values compared to the selection probability values assigned to frequency bin signals having relatively lower magnitudes;
   selecting one frequency bin signal of the reduced set of frequency bin signals by a random process taking into account the selection probability value assigned to the one frequency bin signal of the reduced set of frequency bin signals;
   varying at least one stimulation signal generation parameter used for generating an electrode stimulation signal and affecting a shape of a basic stimulation pulse, the at least one stimulation signal parameter representing a duration of a phase gap between a positive and a negative pulse of a biphasic pulse, wherein varying the at least one stimulation signal generation parameter is a random process; and
   generating the electrode stimulation signal for application to an electrode of the neural auditory prosthesis corresponding to a frequency of the selected frequency bin signal, the generating of the electrode stimulation signal using the at least one stimulation signal generation parameter subject to variations.

9. An auditory stimulation signal processing device comprising:

a plurality of signal inputs configured to receive a plurality of frequency bin signals;

a sorter configured to select a reduced set of frequency bin signals from the plurality of frequency bin signals depending on magnitudes of the plurality of frequency bin signals, the reduced set of frequency bin signals having fewer frequency bin signals than the plurality of frequency bin signals;

a selection probability value assigner configured to assign a selection probability value to each of the reduced set of frequency bin signals depending on each of the reduced set of frequency bin signals, wherein the selection probability value assigner assigns higher-valued selection probability values to frequency bin signals having relatively higher magnitudes with respect to other frequency bin signals of the reduced set of frequency bin signals compared to the selection probability values assigned by the selection probability value assigner to frequency bin signals having relatively lower magnitudes;

a random selector configured to randomly select one frequency bin signal from the plurality of frequency bin signals by a random process taking into account the selection probability value assigned to the one frequency bin signal of the reduced set of frequency bin signals;

a parameter modifier configured to vary at least one stimulation signal generation parameter used for generating an electrode stimulation signal and affecting a shape of a basic stimulation pulse, the at least one stimulation signal parameter representing a duration of a phase gap between a positive and a negative pulse of a biphasic pulse, the parameter modifier including a randomizer for randomizing the varying of the at least one stimulation signal generation parameter; and an electrode stimulation signal generator configured to generate the electrode stimulation signal for application to an electrode of a neural auditory prosthesis, the electrode stimulation signal corresponding to a frequency of the selected frequency bin signal.

10. The auditory stimulation signal processing device according to claim 9, wherein a template for creating the electrode stimulation signal comprises a temporal gap in which the template is substantially zero between two-substantially non-zero sections, and wherein the stimulation signal generation parameter subject to variations is a duration of the temporal gap.

11. The auditory stimulation signal processing device according to claim 9, further comprising an amplitude equalizer configured to perform an amplitude equalization on the received plurality of frequency bin signals.

12. The auditory stimulation signal processing device according to claim 11, wherein:

the amplitude equalizer is further configured to determine whether one electrode of the neural auditory prosthesis had been selected for stimulation during at least one previous stimulation cycle among a certain number of previous stimulation cycles and to attenuate a corresponding frequency bin signal that corresponds to the determined electrode selected for stimulation during the at least one previous stimulation cycle among the certain number of previous stimulation cycles; and the amplitude equalizer is configured to attenuate the corresponding frequency bin for a current stimulation cycle by a predetermined amount.

13. The auditory stimulation signal processing device according to claim 9, wherein the plurality of signal inputs are connectable to a filter bank, the filter bank being based on a simulation of at least one of a basilar membrane and an inner hair cell.

* * * * *